(12) United States Patent
Tietsort et al.

(10) Patent No.: US 10,639,271 B1
(45) Date of Patent: May 5, 2020

(54) FINISHING POWDER FOR USE IN SPRAY TANNING AND METHOD OF ITS USE

(71) Applicants: Erin Tietsort, Bixby, OK (US); Jennifer Roudabush, Tahlequah, OK (US)

(72) Inventors: Erin Tietsort, Bixby, OK (US); Jennifer Roudabush, Tahlequah, OK (US)

(*) Notice: Subject to any disclaimer, the term of this patent is extended or adjusted under 35 U.S.C. 154(b) by 0 days.

(21) Appl. No.: 16/418,290

(22) Filed: May 21, 2019

Related U.S. Application Data

(63) Continuation of application No. 16/240,137, filed on Jan. 4, 2019.

(60) Provisional application No. 62/613,636, filed on Jan. 4, 2018.

(51) Int. Cl.
| | |
|---|---|
| *A61K 8/26* | (2006.01) |
| *A61K 8/9794* | (2017.01) |
| *A61K 8/04* | (2006.01) |
| *A61Q 19/04* | (2006.01) |
| *A61K 8/02* | (2006.01) |

(52) U.S. Cl.
CPC ............ *A61K 8/9794* (2017.08); *A61K 8/022* (2013.01); *A61K 8/046* (2013.01); *A61K 8/26* (2013.01); *A61Q 19/04* (2013.01); *A61K 2800/30* (2013.01); *A61K 2800/43* (2013.01); *A61K 2800/87* (2013.01)

(58) Field of Classification Search
CPC ........ A61K 8/9794; A61K 8/046; A61K 8/26; A61K 8/022; A61K 2800/43; A61K 2800/30; A61K 2800/87; A61Q 19/04
See application file for complete search history.

(56) References Cited

U.S. PATENT DOCUMENTS

2015/0139928 A1* 5/2015 Turmelle ................ A61K 8/25
424/69

OTHER PUBLICATIONS

Callaghan, What Is Powder Used for After a Spray Tan Application? | Spray Tan Class, Oct. 21, 2017, www.youtube.com/watch?v=3j6Aq8MANRM&t=307s (Year: 2017).*
Howtobearedhead, 7 Products to Replace Johnson & Johnson'S Baby Powder, Mar. 7, 2016, hweb.archive.org/web/20160310052318/https://howtobearedhead.com/7-products-to-replace-johnson-johnsons-baby-powder/, pp. 1-6. (Year: 2016).*

* cited by examiner

*Primary Examiner* — Ali Soroush
(74) *Attorney, Agent, or Firm* — Gable Gotwals

(57) ABSTRACT

Embodiments of a finishing powder of this disclosure include a rice powder and an iron-oxide pigment, with no talc or parabens, that eliminates transfer of wet or sticky spray tan bronzer to clothing, hands, or between opposing folds or creases of skin. The finishing powder may be applied full body—for example 85% to 95% of total body surface area—by way of a brush, being too thick in its consistency to spray. The powder may be blown from the brush to the body. An amount of the mixture applied to a user may be in a range ¾ teaspoon to 2¼ teaspoon. The powder immediately coats the spray tanning solution and remains dry to the touch. Because of its thicker consistency, the powder does not dissipate and remains on the skin up to 24 hours or until the user showers.

12 Claims, 1 Drawing Sheet

FINISHING POWDER FOR USE IN SPRAY TANNING AND METHOD OF ITS USE

CROSS-REFERENCE TO CO-PENDING APPLICATIONS

This application is a continuation application of U.S. patent application Ser. No. 16/240,137, filed Jan. 4, 2019, which claims priority to U.S. Provisional Patent Application No. 62/613,636, titled Finishing Powder for Use in Spray Tanning, filed Jan. 4, 2018, the subject matter of which are incorporated herein by reference.

BACKGROUND

This disclosure is in the field of spray tanning and, more particularly, compositions intended for use after a spray tanning bronzer is applied.

Spray tanning is a form of lightless tanning, either sunless or not using ultraviolet lights. During spray tanning, a bronzer in the form of a fine mist containing dihydroxyacetone or DHA is sprayed onto an individual. The bronzer interacts with skin chemistry to turn the skin a bronze-like color. Until the bronzer dries or sets, the bronzer remains tacky or sticky and may adhere to unwanted skin areas clothes or other objects that the spray-tanned individual comes into contact with. The bronzer typically remains sticky for at least one or two hours after application and may become less sticky in a range of two to eight hours, but will always remain somewhat tacky during this process unless powder is applied. The bronzer typically requires a minimum of 8 hours to 10 hours to fully set. In an attempt to solve the sticky problem, various powders have been developed for application after spray tanning.

Prior to application to those areas of the body where powder is to be applied, the spray tan on those areas requires air drying with a fan or air from the spray tan gun for about 1 to 2 minutes (with the remaining areas of the body remaining sticky). For example, U.S. Pat. No. 8,974,773 B2 to Turmelle discloses a talc-based spray tan drying powder which is applied during the drying stage to "creases" where opposing skin surfaces may come into contact with one another such as creases (e.g. inside of the elbows, behind the knees, beneath bottom checks, under the arms). A commercial embodiment of this powder is marketed as TAN IN THE RAW™ powder. Another drying powder, CALIFORNIA TAN® powder is a corn starch-based spray tan drying powder that includes kaolin clay and coffee. These powders are very fine, are applied using a powder puff (in a blotting or pounding movement substantially normal to the wet skin surface) or spray bottle, and typically dissipate or absorb completely within one to two hours (at most) of application. Once the powder dissipates or absorbs, the bronzer remains sticky as it still sets, and the tanning odor returns.

SUMMARY

The consistency and make-up of embodiments of a finishing powder of this disclosure, and the way these embodiments are applied to the body surface area of a client covered or coated with a spray tan solution, fundamentally changes spray tanning practice because it enables a spray tan client to get dressed immediately after a spray tanning session without worry of the bronzer transferring to clothing. Unlike before, where most spray tanning was done in the evening (e.g. the 5:00 p.m. to 11:00 p.m. after-work window) and the client had to go straight home and allow the spray tan solution to dry, the client may now spray tan at any time of the day and immediately continue on with their daily activities (outside of activities that cause above normal perspiration levels like rigorous exercise). The powder does not dissipate or absorb within an hour or two after application like prior art powders, remains on the skin up to 24 hours prior to washing with water, causes the spray tan to feel more comfortable to the client as it is developing, and continues to control odor as well as mild perspiration. In experiments conducted by the inventors, the powder remained on the skin longer than 24 hours. No adverse dermatological effects are observed.

Embodiments of a spray tan finishing powder of this disclosure are a hypoallergenic, talc and paraben free, unique blend of cosmetic grade powders and micas that were designed to be used in conjunction with spray tan formulas. The finishing powder coats the spray tan formula but does not chemically react with the formula. In some embodiments, the powder has a very light shimmer and, in other embodiments, the powder has a matte finish with no shimmer. Immediately following a spray tan, the powder is applied full body and the client can get dressed, feeling completely dry. The bronzer from the spray tan does not transfer to clothes or car seats like it has in the past, nor does it transfer skin-to-skin when one part of the body contacts another part, like creases. The finishing powder helps set the spray tan while the spray tan is developing, which means less mess ups and fewer complaints. The powder eliminates that post-spray sticky feeling, leaving a shimmer and a fresh scent.

Embodiments of a finishing powder of this disclosure include a rice powder and an iron-oxide pigment, with no talc or parabens. The powder eliminates transfer of wet or sticky spray tan bronzer to clothing, hands, or between opposing folds or creases of skin. The finishing powder is made to be applied to the full body—for example 85% to 95% of total body surface area—by way of a very soft brush. In embodiments, the brush is a loose, long hair, fan brush. The powder cannot be applied by a powder puff or with sprayers of a kind known in the art. An amount of the mixture applied may be in a range ¾ teaspoon to 2¼ teaspoon. By applying the finishing powder to the body surface area coated with spray tan solution (which includes a bronzer), the spray tan solution immediately dries, setting the spray tan.

Additionally, embodiments of the finishing powder may be used as a dry shampoo and as a deodorant.

DETAILED DESCRIPTION

Figure 2:
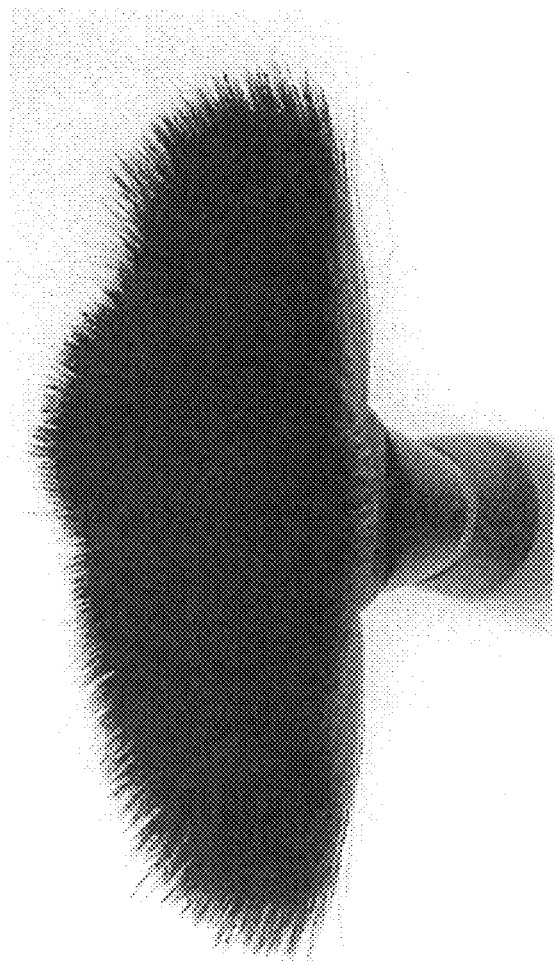
FIG. 2 is a top isometric view photograph of the brush of FIG. 2.
Figure 1:
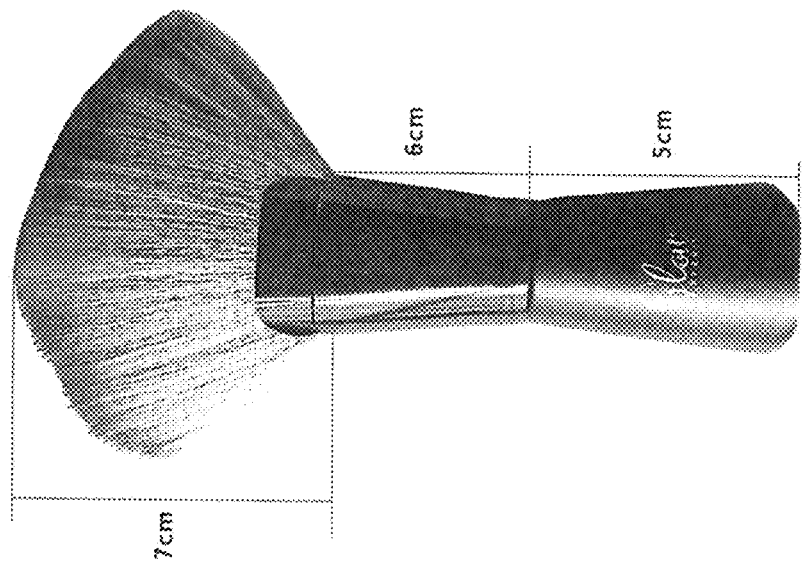
FIG. 1 is a front elevation view photograph of an embodiment of a brush of this disclosure. In embodiments, brush is a loose, long hair, fan brush. The thickness of the brush hair at its thickest point in the middle may be 4 cm. The width of the fanned hair may be 12 cm.

In embodiments of a finishing powder of this disclosure, the finishing powder includes a rice powder and an iron oxide pigment or its equivalent. The finishing powder is paraben-free and talc-free. Embodiments do not include corn-starch, clays, or coffee products. The finishing powder may be scented with a natural or artificial scent (fragrant) or left unscented. The finishing powder may include mica for shimmer or instead have a matte (flat) appearance. In embodiments, the color or shade of the finishing powder is lighter than that of the bronzer used in the spray tanning. The shade may be adjusted, for example, depending on such factors as the bronzer shade, the user's skin tone or color, and the combination of the two. For example, the spray tan bronzer may be a first shade and the mixture is of a second lighter shade.

The finishing powder is intended for full body application and may be brushed directly on the skin after the spray tan solution is air-dried for 1-2 minutes. The skin or bronzer will still be sticky, but applying the powder will not damage the spray tan. The typical application of powder may be in a range of 45% to 95% of total body surface area. See e.g. Table 2 below. In embodiments, the density of the finishing powder may be in a range of 0.05 ounces to 0.10 ounces per teaspoon (0.29 g/ml to 0.58 g/ml), for example, 0.083 ounces per teaspoon (0.477 g/ml). The finishing powder may be applied in a range of ¾ teaspoon (3.7 ml) to 2¼ teaspoons (11.1 ml) of powder per full body application, there being subranges within this broader range. In some embodiments, 1 teaspoon (4.9 ml) may be used, and is the typical amount. In other embodiments, 2 teaspoons (9.8 ml) maximum may be used. The powder remains on the skin and continues to absorb mild perspiration that helps protect the bronzer until it is washed off along with the bronzer, which typically occurs 8 to 10 hours after the spray tanning application. The powder does not appear to react with the bronzer. Rather, the powder coats the bronzer, serving as a kind of shellac or coating for the bronzer.

The previous powders that are only applied to the skin crease areas of the body are made of a much finer grade powder and typically dissipate within an hour or are absorbed by the bronzer. Therefore this kind or consistency of powder does not provide any long lasting anti-sticky or protection of the bronzer on the skin. Body surface area ("BSA") to which the finishing powder of this disclosure is applied may be calculated using known calculations, including but not limited to, the DuBois and DuBois formula:

$$BSA = 0.007184(W^{0.425} \times H^{0.725}) \quad \text{(Eq. 1)}$$

where the weight is in kilograms, the height is in centimeters, and BSA is in square meters.

Using average BSAs as a baseline, the finishing powder may be applied as shown in Table 1. For example, where the finishing powder is applied to 100% of BSA, the finishing powder may be in a range 0.04 teaspoons to 0.13 teaspoons per square foot (2.0 ml to 6.9 ml per square meter), there being subranges within this broader range. The actual distribution may be about this much, that is, within a range of ±1% to ±10 of the nominal value, there being subranges within this broader range. The same is true of the teaspoons or ml per application.

TABLE 1

Application coverage per square foot or square meter for various percentages of full body surface area.

|      |         |     |       | tsp   |       |       |     |      | ml   |      |       |
|------|---------|-----|-------|-------|-------|-------|-----|------|------|------|-------|
| 100% | Average | ft2 | 0.75  | 1.00  | 2.00  | 2.25  | m2  | 3.70 | 4.9  | 9.8  | 11.1  |
|      | Male    | 20.45 | 0.037 | 0.049 | 0.098 | 0.110 | 1.9 | 1.95 | 2.58 | 5.16 | 5.84 |
|      | Female  | 17.22 | 0.044 | 0.058 | 0.116 | 0.131 | 1.6 | 2.31 | 3.06 | 6.13 | 6.94 |
|      | Overall | 18.30 | 0.041 | 0.055 | 0.109 | 0.123 | 1.7 | 2.18 | 2.88 | 5.76 | 6.53 |
| 95%  | Average | ft2 | 0.75  | 1.00  | 2.00  | 2.25  | m2  | 3.70 | 4.9  | 9.8  | 11.1  |
|      | Male    | 19.43 | 0.039 | 0.051 | 0.103 | 0.116 | 1.8 | 2.05 | 2.71 | 5.43 | 6.15 |
|      | Female  | 16.36 | 0.046 | 0.061 | 0.122 | 0.138 | 1.5 | 2.43 | 3.22 | 6.45 | 7.30 |
|      | Overall | 17.39 | 0.043 | 0.058 | 0.115 | 0.129 | 1.6 | 2.29 | 3.03 | 6.07 | 6.87 |
| 90%  | Average | ft2 | 0.75  | 1.00  | 2.00  | 2.25  | m2  | 3.70 | 4.9  | 9.8  | 11.1  |
|      | Male    | 18.41 | 0.041 | 0.054 | 0.109 | 0.122 | 1.7 | 2.16 | 2.87 | 5.73 | 6.49 |
|      | Female  | 15.5  | 0.048 | 0.065 | 0.129 | 0.145 | 1.4 | 2.57 | 3.40 | 6.81 | 7.71 |
|      | Overall | 16.47 | 0.046 | 0.061 | 0.121 | 0.137 | 1.5 | 2.42 | 3.20 | 6.41 | 7.25 |
| 85%  | Average | ft2 | 0.75  | 1.00  | 2.00  | 2.25  | m2  | 3.70 | 4.9  | 9.8  | 11.1  |
|      | Male    | 17.38 | 0.043 | 0.058 | 0.115 | 0.129 | 1.6 | 2.29 | 3.03 | 6.07 | 6.87 |
|      | Female  | 14.64 | 0.051 | 0.068 | 0.137 | 0.154 | 1.4 | 2.72 | 3.60 | 7.21 | 8.16 |
|      | Overall | 15.56 | 0.048 | 0.064 | 0.129 | 0.145 | 1.4 | 2.56 | 3.39 | 6.78 | 7.68 |
| 80%  | Average | ft2 | 0.75  | 1.00  | 2.00  | 2.25  | m2  | 3.70 | 4.9  | 9.8  | 11.1  |
|      | Male    | 16.36 | 0.046 | 0.061 | 0.122 | 0.138 | 1.5 | 2.43 | 3.22 | 6.45 | 7.30 |
|      | Female  | 13.78 | 0.054 | 0.073 | 0.145 | 0.163 | 1.3 | 2.89 | 3.83 | 7.66 | 8.67 |
|      | Overall | 14.64 | 0.051 | 0.068 | 0.137 | 0.154 | 1.4 | 2.72 | 3.60 | 7.21 | 8.16 |
| 75%  | Average | ft2 | 0.75  | 1.00  | 2.00  | 2.25  | m2  | 3.70 | 4.9  | 9.8  | 11.1  |
|      | Male    | 15.34 | 0.049 | 0.065 | 0.130 | 0.147 | 1.4 | 2.60 | 3.44 | 6.88 | 7.79 |
|      | Female  | 12.92 | 0.058 | 0.077 | 0.155 | 0.174 | 1.2 | 3.08 | 4.08 | 8.17 | 9.25 |
|      | Overall | 13.73 | 0.055 | 0.073 | 0.146 | 0.164 | 1.3 | 2.90 | 3.84 | 7.69 | 8.71 |

The finishing powder may be applied to at least 45%, 50%, 55%, 60%, 65% 70%, 75%, 80%, 85%, 90%, 95%, and 99% of BSA, there being values and subranges within this broader range. In embodiments, the finishing powder is applied to virtually all body surface area, for example, 80% to 95%, 85% to 95%. For purposes of this disclosure, the values shown in Table 2 may be used to determine the portion of total BSA to which the finishing powder is applied: For example, application of the finishing powder to the anterior (9%) and posterior (9%) of each leg (2×18%) and to the anterior (4.5%) and posterior (4.5%) of each arm (2×9%) results in 54% coverage (36%+18%). Further applying the finishing powder to the anterior (18%) and posterior (18%) torso results in 90% coverage (54%+36%). Applying the powder to the face increases the coverage to almost 95%.

TABLE 2

Approximate percentage of body surface area provided by various anatomic structures.

| Anatomic structure | Approximate % of body surface area |
|---|---|
| Anterior head | 4.5 |
| Posterior head | 4.5 |
| Anterior torso | 18 |
| Posterior torso | 18 |
| Anterior leg, each | 9 |
| Posterior leg, each | 9 |
| Anterior arm, each | 4.5 |
| Posterior arm, each | 4.5 |

By way of a non-limiting example, and using weight, 1 ounce (28.3 g) of the powder of this disclosure may be effective for 12 applications (e.g. 0.083 ounces per application; 6 ounces or 170 g for 72 full body applications, 1 pound or 454 g for 192 full body applications; 2 pounds or 907 g for 384 applications). In other embodiments, the powder may be effective in a range of 1 ounce (28.3 g) per 10 to 14 applications (0.07 ounces to 0.10 ounces per application; 0.202 g to 0.283 g per application). A calculation similar to that of Table 1 may be used to determine density or weight of coverage per square foot or square meter. An application may be in a range of 75% to 95% (virtually all) of BSA. The rice powder used in embodiments may be an oryza sativa powder or its equivalent. The iron oxide pigment may include a mica for shimmer or glimmer such as a silicate (phyllosilicate) mineral and titanium dioxide. The titanium dioxide may be titanium white, pigment white 6, or CI 77891. A zinc oxide may also be used.

The oryza sativa powder may be in a range of about 80% wgt. to 90% wgt., 85% wgt. to 90% wgt., 86% wgt. to 89% wgt., 87% wgt. to 88% wgt., or 87% wgt.; The iron oxide pigment may be in a range of about 5% wgt. to 15% wgt., 6% wgt. to 14% wgt., 7% wgt. to 13% wgt., 8% wgt. to 12% wgt., 9% wgt. to 11% wgt., or 10% wgt. The scent may be in a range of about 1% wgt. to 5% wgt., 2% wgt. to 4% wgt., 2½% wgt. to 3½% wgt., or 3% wgt. In unscented embodiments, the weight percentages of the oryza sativa powder and iron oxide pigment are adjusted accordingly as a percent of total weight. For example, the oryza sativa powder may be in a range of 80% wgt. to 95% wgt. and the iron oxide pigment may be in a range of 5% wgt. to 20% wgt.

When applied after a spray tanning, the finishing powder helps set the spray tan while the spray tan is developing; eliminates the post-spray, sticky feeling; and prevents the bronzer from adhering to clothing or other objects. Before applying the powder, the skin may be air dried using a fan or a blower for 30 seconds, 1 minute, 1½ minutes, 2 minutes, 2½ minutes, 3 minutes, or in a range of 30 seconds to 3 minutes, there being subranges within this broader range.

Embodiments of a finishing powder of this disclosure cannot be sprayed using sprayers known in the art to apply cosmetic powders because its consistency is too thick. The finishing powder is a thicker or more dense powder than the prior art powders. The prior art powders are very fine and can be sprayed through a spray nozzle of a kind known in the spray tanning and cosmetic arts. However, these finer powders dissipate, rub or flake off, and do not remain on the skin. A finishing powder of this disclosure, with its thicker consistency, effectively coats the skin and remains on the skin until the client showers.

The powder is applied by brush A powder puff is not used, nor is a spray bottle. In some embodiments, the brush is a soft, non-abrasive brush such as a loose-haired fan brush. The brush hair may be synthetic hair or its equivalent. The brush may be used to brush the finishing powder onto the spray tan. In some embodiments, the powder may be applied to the brush and an air sprayer may be used to blow the powder from the brush to the skin. In yet other embodiments a combination of brushing and blowing the powder from the brush may be used.

Embodiments of a method of this disclosure, for setting a spray tan bronzer on a body, include:
  applying, to a fan brush, a spray tan finishing powder including oryza sativa powder and a pigment, the oryza stative powder being in a range of 80% wgt. to 95% wgt, the pigment being in a range of 5% wgt. to 20% wgt, the spray tan finishing powder being too thick in its consistency to spray;
  transferring the spray tan finishing powder from the fan brush to the body; and
  reapplying the spray tan finishing powder to the fan brush, as needed, for subsequent transferring.

The spray tan finishing powder covers about 45% to 95% of body surface area after the transferring and remains on the body—not dissipated, rubbed off, or absorbed—prior to washing with water, at least 4 hours, 5 hours, 6 hours, 7 hours, in a range of 4 hours to 8 hours, or in a range of 8 hours to 24 hours, there being ranges and subranges within these broader ranges. An overall amount of the spray tan finishing powder transferred to the body is in a range ¾ teaspoon to 2¼ teaspoons. The transferring may include an air sprayer, the air sprayer blowing the spray tan finishing powder from the fan brush to the body. Prior to the applying, air drying the spray tan bronzer in a range of 30 seconds to 3 minutes may be used. The air drying may include forced air.

Embodiments of a spray tan bronzer setting system of this disclosure include a fan brush and a spray tan finishing powder including oryza sativa powder and a pigment, the oryza sativa powder being in a range of 80% wgt. to 95% wgt, the pigment being in a range of 5% wgt. to 20% wgt, the spray tan finishing powder being too thick in its consistency to spray. As with embodiments of the method, the spray tan finishing powder is applied to the fan brush and then transferred from the fan brush to about 45% to 95% of body surface area; the 45% to 95% of the body surface area covered by a not-yet-set spray tan bronzer. The overall amount of the spray tan finishing powder transferred from the fan brush to the body is in a range of ¾ teaspoon to 2¼ teaspoons, the powder remains on the body, prior to washing with water, at least 4 hours, 5 hours, 6 hours, 7 hours, in a range of 4 hours to 8 hours, or in a range of 8 hours to 24 hours, there being ranges and subranges within these broader ranges. The system may also include an air sprayer, the air sprayer configured to blow the spray tan finishing powder from the fan brush to the body surface area.

While embodiments of a finishing powder have been described in detail, modifications may be made to the powder and its method of application without departing from the scope of this disclosure and the following claims.

The claims include the full range of equivalents to which each recited element is entitled.

The invention claimed is:

1. A method for setting a spray tan bronzer on a body, the method comprising:
    applying, to a fan brush, a spray tan finishing powder including oryza sativa powder and a pigment, the oryza sativa powder being in a range of 90% wgt. to 95% wgt, the pigment being in a range of 5% wgt. to 10% wgt, the spray tan finishing powder being too thick in its consistency to spray;
    transferring the spray tan finishing powder from the fan brush to the body; and
    reapplying the spray tan finishing powder to the fan brush, as needed to set the spray tan bronzer, for subsequent transferring of the spray tan finishing powder from the fan brush to the body;
    after the transferring, the spray tan finishing powder forming a coating over the spray tan bronzer, the spray tan bronzer setting underneath the coating, the spray tan finishing powder covering about 80% to 95% of body surface area after the transferring and remaining on the body surface area, prior to washing with water, in a range of 4 hours to 24 hours;
an overall amount of the spray tan finishing powder transferred to the body being in a range of ¾ teaspoon to 2¼ teaspoons.

2. A method according to claim 1, wherein prior to the transferring, air drying the spray tan bronzer in a range of 30 seconds to 3 minutes.

3. A method according to claim 1, the air drying including forced air.

4. A method according to claim 1, wherein the spray tan bronzer is of a first shade and the spray tan finishing powder is of a second lighter shade.

5. A method according to claim 1, wherein the spray tan finishing powder includes a fragrant in a range of 1% wgt. to 5% wgt.

6. A method according to claim 1, wherein the pigment contains mica.

7. A method according to claim 1, wherein the pigment does not contain mica.

8. A method according to claim 1, wherein the spray tan finishing powder does not include talc.

9. A method according to claim 1, wherein the spray tan finishing powder does not include a paraben.

10. A method for setting a spray tan bronzer on a body, the method comprising:
    applying, to a brush, a spray tan finishing powder consisting of oryza sativa powder, a pigment, and a fragrant, the oryza sativa powder being in a range of 90% wgt. to 95% wgt.;
    transferring the spray tan finishing powder from the brush to the body; and
    reapplying the spray tan finishing powder to the brush, as needed to set the spray tan bronzer, for subsequent transferring of the spray tan finishing powder from the brush to the body;
    after the transferring, the spray tan finishing powder covering about 80% to 95% of body surface area after the transferring and remaining on the body surface area, prior to washing, in a range of 4 hours to 24 hours;
an overall amount of the spray tan finishing powder transferred to the body being in a range of ¾ teaspoon to 2¼ teaspoons.

11. The method of claim 10, wherein the spray tan finishing powder is transferred in an amount sufficient for the spray tan finishing powder to form a coating over the spray tan bronzer and the spray tan bronzer is allowed to set underneath the coating.

12. The method of claim 11, wherein the spray tan finishing powder is transferred to the body using a fan brush.

* * * * *